United States Patent [19]

Abrams et al.

[11] Patent Number: 5,041,381
[45] Date of Patent: Aug. 20, 1991

[54] MONOCLONAL ANTIBODIES AGAINST HUMAN INTERLEUKIN-4 AND HYBRIDOMAS PRODUCING THE SAME

[75] Inventors: John S. Abrams, Belmont, Calif.; Isabelle Chretien, Ecully, France; Frank D. Lee, Palo Alto, Calif.

[73] Assignee: Schering Corporation, Kenilworth, N.J.

[21] Appl. No.: 113,623

[22] Filed: Oct. 26, 1987

Related U.S. Application Data

[63] Continuation-in-part of Ser. No. 881,553, Jul. 3, 1986, which is a continuation-in-part of Ser. No. 843,958, Mar. 25, 1986, abandoned, which is a continuation-in-part of Ser. No. 799,668, Nov. 19, 1985, abandoned.

[51] Int. Cl.$^5$ .................. C07K 15/28; C12N 5/20; G01N 33/543; G01N 33/535
[52] U.S. Cl. .................. 435/240.27; 530/387; 530/413; 935/104; 935/108; 935/110; 436/518; 435/7
[58] Field of Search .................. 533/387; 435/240.27; 435/7; 530/413; 436/518; 935/104, 108, 110

[56] References Cited

U.S. PATENT DOCUMENTS 4,431,739  2/1984  Riggs .................. 435/253

OTHER PUBLICATIONS

Sahasrabuddhe et al., pp. 463–473 in "Immune Regulation by Characterized Polypeptides U.C.L.A. Symp. Mol. & Cell Biology New Series" vol. 41 Alan R. Liss Inc. 5/87 Goldstein et al. Eds.
Kipps et al., p. 108.1–108.9 in Handbook of Expt'l Immunology vol. 4.
Weir et al., Eds., Blackwell Sci. Publ. 1986.
Ohara et al., Nature 315: 333–336 1985.
Yokota et al. PNAS 83:5894–5898, 1986.
Mehta et al., J. Immunology 135: 3298–3302, 1985.
Morrison Science 229: 1202, 1985.
Williams et al., pp. 22.1–22.24 in Handbook of Exptl. Immunology vol. 1, Weir et al. Eds. Blackwell Sci. Publ. 1986.
Howard et al., Immunol. Rev. 78: 185 1984.
Sharma et al., Science, vol. 235, pp. 1489–1492 (1987).

Primary Examiner—Margaret Moskowitz
Assistant Examiner—Paula Hutzell
Attorney, Agent, or Firm—Stephen C. Macevicz

[57] ABSTRACT

Monoclonal antibodies are provided which are specific for human interleukin-4. Kits and methods are also provided for detecting, measuring and immunopurifying human interleukin-4.

2 Claims, 1 Drawing Sheet

MONOCLONAL ANTIBODIES AGAINST HUMAN INTERLEUKIN-4 AND HYBRIDOMAS PRODUCING THE SAME

CROSS REFERENCE TO RELATED APPLICATIONS

This application is a continuation-in-part of copending application Ser. No. 881,553 filed July 3, 1986, which is a continuation-in-part of copending application Ser. No. 843,958 filed Mar. 25, 1986, now abandoned which is a continuation-in-part of application Ser. No. 799,668 filed Nov. 19, 1985, now abandoned.

FIELD OF THE INVENTION

The invention relates generally to monoclonal antibodies and their associated hybridomas, and more particularly, to monoclonal antibodies specific for human interleukin-4.

BACKGROUND

Human interleukin-4 (IL-4) was first cloned and characterized by Yokota et al., *Proc. Natl. Acad. Sci.*, Vol. 83, pgs. 5894–5898 (1986). IL-4 is a highly pleiotropic lymphokine which affects many different components of the immune system. It has T cell growth factor (TCGF) activity; and B cell growth factor activity. It is capable of potentiating the TCGF activity of interleukin-2 (IL-2) and the colony forming activity of granulocyte-macrophage colony stimulating factor. It induces the preferential production of $IgG_1$ and IgE, and induces the expression of human leukocyte class II DR antigens. These activities suggest several possible therapeutic uses, e.g. as a potentiating agent for IL-2 anticancer therapy, as a potentiating agent for GM-CSF stimulated bone marrow regeneration, or as an agent to treat bare lymphocyte syndrome, Touraine, *Lancet*, pgs. 319–321 (Feb. 7, 1981); Touraine and Betuel, *Human Immunology*, Vol. 2, pgs. 147–153 (1981); and Sullivan et al., *J. Clin. Invest.*, Vol. 76, pgs. 75–79 (1985).

An important aspect of any therapy involving drugs is the ability to predict and/or monitor concentration levels in the blood or other patient body fluids. Monoclonal antibodies are widely used for this purpose, e.g. Springer, ed., *Hybridoma Technology in the Biosciences and Medicine* (Plenum Press, N.Y., 1985); and U.S. Pat. Nos. 4,562,003; 4,486,530; and 4,255,329.

In the production of genetically engineered proteins such as IL-4, separation of the expressed protein from the transformed host cells and/or their culture supernatants is a major problem. Frequently separation procedures involve one or more passes of crude material through immunoadsorbent columns. Monoclonal antibodies specific for the protein to be purified are crucial elements of such columns. Such monoclonal antibodies can also be used to measure the degree of purification achieved by a particular protocol, e.g. by "Western" blot analysis, Burnette, *Anal. Biochem.*, Vol. 112, pgs. 195–203 (1981).

From the foregoing it is evident that the availability of monoclonal and/or polyclonal antibodies specific for IL-4 could facilitate medical and veterinary applications of the compound by improving current methods of purification, and by providing means for monitoring concentrations of IL-4 in body fluids, such as blood, urine, or the like.

SUMMARY OF THE INVENTION

The invention provides compounds and compositions useful for the detection, purification, measurement and/or inhibition of human IL-4. The compounds and compositions are derived from hybridomas producing monoclonal antibodies specific for human IL-4. The compounds and compositions of the invention include the hybridomas themselves, monoclonal antibodies produced by the hybridomas, heavy chain and light chain variable region polypeptides thereof, and other fragments thereof, such as half-molecules comprising a light chain joined to a heavy chain by natural disulfide bonds, Fab fragments, F(ab)$_2$ fragments, Fv fragments, and the like. The invention also includes methods of using the above compounds and compositions to detect, purify, and measure the concentration of human IL-4, and kits for practicing such methods. In particular, the invention includes hybridoma IC1.11B4.6 and its monoclonal antibody and products derived therefrom.

Compositions of the invention may also be useful as agonists or antagonists of human IL-4. In particular, compositions comprising fragments of antagonistic anti-IL-4 antibodies are useful therapeutic agents for treating atopic diseases.

Compositions of the invention also include messenger RNA (mRNA) extracted from hybridoma IC1.11B4.6. Such mRNAs are useful in cloning and expressing fragments of the IC1.11B4.6 antibody in bacteria, yeast, or other hosts.

Antibodies comprise an assembly of polypeptide chains linked together by disulfide bridges. Two major polypeptide chains, referred to as the light chain and the heavy chain, make up all major structural classes (isotypes) of antibody. Both heavy chains and light chains are further divided into subregions referred to as variable regions and constant regions. Heavy chains comprise a single variable region and three different constant regions, and light chains comprise a single variable region (different from that of the heavy chain) and a single constant region (different from those of the heavy chain). The variable regions of the heavy chain and light chain are responsible for the antibody's binding specificity.

As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid.

The terms Fab, Fc, F(ab)$_2$, and Fv are employed with their standard immunological meanings, e.g. Klein, *Immunology* (John Wiley, New York, 1982) or Parham, Chapter 14, in Weir, ed. *Immunochemistry*, 4th Ed. (Blackwell Scientific Publishers, Oxford, 1986).

As used herein the term "monoclonal antibody" refers to homogenous populations of immunoglobulins which are capable of specifically binding to human IL-4. It is understood that human IL-4 may have one or more antigenic determinants comprising (1) peptide antigenic determinants which consist of single peptide chains within human IL-4, (2) conformational antigenic determinants which consist of more than one spacially contiguous peptide chains whose respective amino acid sequences are located disjointly along the human IL-4 polypeptide sequence; and (3) posttranslational antigenic determinants which consist, either in whole or part, of molecular structures covalently attached to human IL-4 after translation, such as carbohydrate groups, or the like. The antibodies of the invention may be directed against one or more of these determinants.

As used herein the term "binding composition" means a composition comprising two polypeptide chains (1) which, when operationally associated, assume a conformation having high binding affinity for human interleukin-4, and (2) which are derived from a hybridoma producing monoclonal antibodies specific for human interleukin-4. The term "operationally associated" is meant to indicate that the two polypeptide chains can be positioned relative to one another for binding by a variety of means, including by association in a native antibody fragment, such as Fab or Fv, or by way of genetically engineered cysteine-containing peptide linkers at the carboxyl termini. Normally, the two polypeptide chains correspond to the light chain variable region and heavy chain variable region of a monoclonal antibody specific for human interleukin-4.

DETAILED DESCRIPTION OF THE INVENTION

Figure 1:
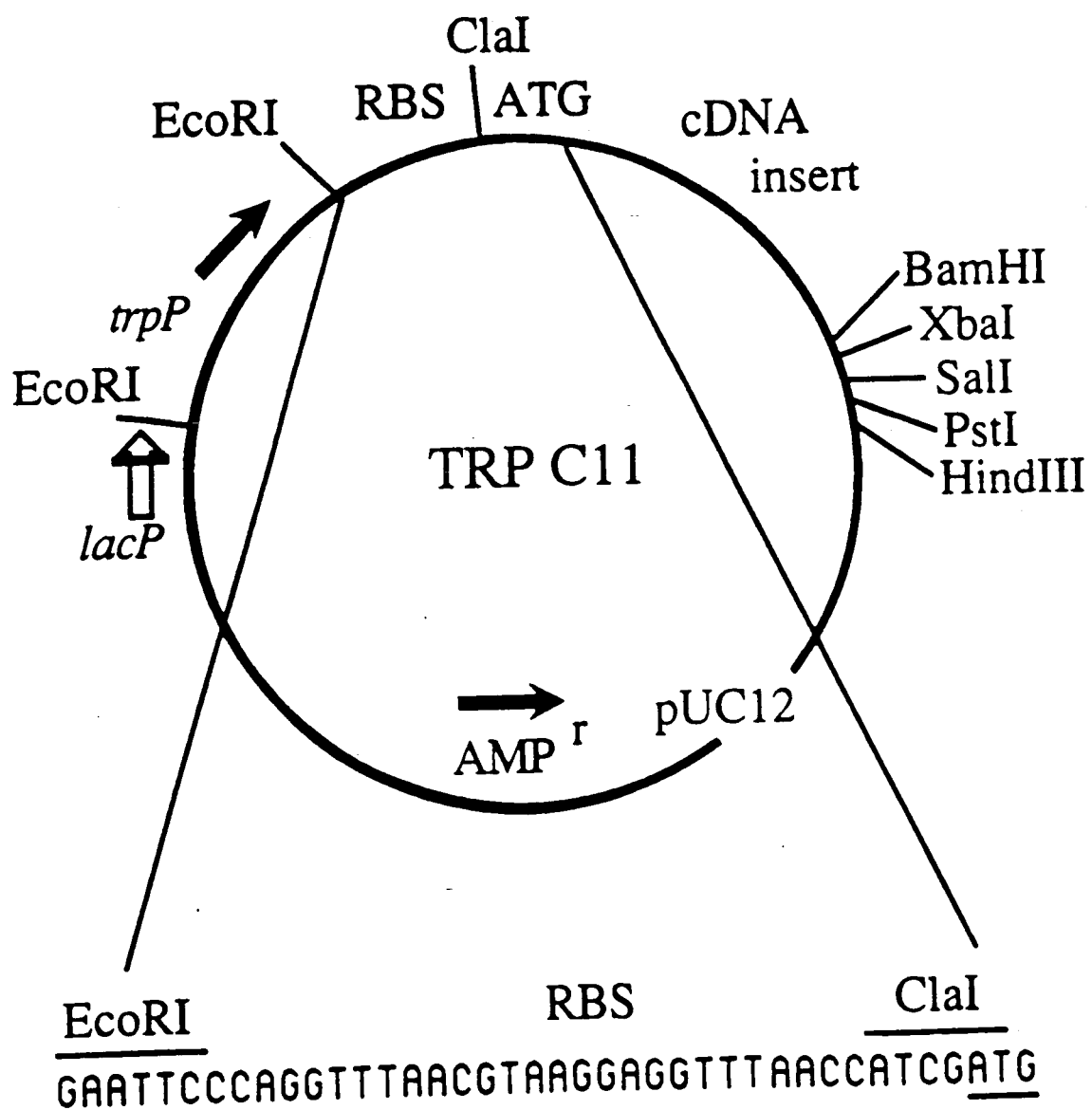
FIG. 1 is a diagrammatic representation of an expression vector suitable for expressing unglycosylated human IL-4 in a bacterial host.

Hybridomas of the invention are produced by well known techniques. Usually, the process involves the fusion of an immortalizing cell line with a B-lymphocyte which produces the desired antibody. Alternatively, non-fusion techniques for generating an immortal antibody producing cell lines are possible, and come within the purview of the present invention, e.g. virally induced transformation: Casali et al., "Human Monoclonals from Antigen-Specific Selection of B Lymphocytes and Transformation by EBV," Science, Vol. 234, pgs. 476-479 (1986). Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining the appropriate lymphocytes from mammals injected with the target antigen are well known. Generally, either peripheral blood lymphocytes (PBLs) are used if cells of human origin are desired, or spleen cells or lymph node cells are used if non-human mammalian sources are desired. A host mammal is injected with repeated dosages of the purified antigen, and the mammal is permitted to generate the desired antibody producing cells before these are harvested for fusion with the immortalizing cell line. Techniques for fusion are also well known in the art, and in general, involve mixing the cells with a fusing agent, such as polyethylene glycol. Hybridomas are selected by standard procedures, such as HAT selection. From among these hybridomas, those secreting the desired antibody are selected by assaying their culture medium by standard immunoassays, such as Western blotting, ELISA, RIA, or the like. Antibodies are recovered from the medium using standard protein purification techniques, e.g. Tijssen, Practice and Theory of Enzyme Immunoassays (Elsevier, Amsterdam, 1985).

Many references are available for guidance in applying any of the above techniques, e.g. Kohler et al., Hybridoma Techniques (Cold Spring Harbor Laboratory, New York, 1980); Tijssen, Practice and Theory of Enzyme Immunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, FL, 1982); and the like.

The use and generation of fragments of antibodies is also well known, e.g. Fab fragments: Tijssen, Practice and Theory of Enzyme Immunoassays (Elsevier, Amsterdam, 1985); and Fv fragments: Hochman et al. Biochemistry, Vol. 12, pgs. 1130-1135 (1973), Sharon et al., Biochemistry, Vol. 15, pgs. 1591-1594 (1976) and Ehrlich et al., U.S. Pat. No. 4,355,023; and antibody half molecules: Auditore-Hargreaves, U.S. Pat. No. 4,470,925. Moreover, such compounds and compositions of the invention can be used to construct bi-specific antibodies by known techniques, e.g., via further fusions of hybridomas (i.e. to form so-called quadromas), Reading, U.S. Pat. No. 4,474,493; or via chemical reassociation of half molecules, Brennan et al., Science, Vol. 229, pgs. 81-83 (1985).

Hybridomas and monoclonal antibodies of the invention are produced against either glycosylated or unglycosylated versions of recombinantly produced mature human interleukin-4. Generally, unglycosylated versions of human IL-4 are produced in E. coli, and glycosylated versions are produced in mammalian cell hosts, e.g. CV1 or COS monkey cells, mouse L cells, or the like. Recombinantly produced mature human IL-4 is produced by introducing an expression vector into a host cell using standard protocols, e.g. Maniatis et al., Molecular Cloning: A Laboratory Manual (Cold Spring Harbor Laboratory, New York, 1982); Okayama and Berg, Mol. Cell. Biol., Vol. 2, pgs. 161-170 (1982) and Vol. 3, pgs. 280-289 (1983); Hamer, Genetic Engineering, Vol. 2, pgs. 83-100 (1980) and U.S. Pat. No. 4,599,308; Kaufman et al., Mol. Cell. Biol., Vol. 2, pgs. 1304-1319 (1982); or the like.

Construction of bacterial or mammalian expression vectors are well known in the art, once the nucleotide sequence encoding a desired protein is known or otherwise available, e.g. DeBoer in U.S. Pat. No. 4,551,433 discloses promoters for use in bacterial expression vectors; Goeddel et al., in U.S. Pat. No. 4,601,980, and Riggs, in U.S. Pat. No. 4,431,739 disclose the production of mammalian proteins by E. coli expression systems; and Riggs (cited above), Ferretti et al., Proc. Natl. Acad. Sci., Vol. 83, pgs. 599-603 (1986), Sproat et al., Nucleic Acids Research, Vol. 13, pgs. 2959-2977 (1985), and Mullenbach et al., J. Biol. Chem., Vol. 261, pgs. 719-722 (1986) disclose how to construct synthetic genes for expression in bacteria. Accordingly, these references are incorporated by reference. The amino acid sequence of mature human IL-4 is disclosed by Yokota et al. (cited above), and the cDNA encoding human IL-4 carried by the pcD vector described in Yokota et al. (cited above) is deposited with the American Type Culture Collection (ATCC), Rockville, MD, under accession number 67029. Many bacterial expression vectors and hosts are available commercially and through the ATCC. Preferably, human IL-4 for immunizing host animals is isolated from culture supernatants of COS, CV1, or mouse L cells which have been transiently transfected by the above-mentioned pcD vector.

Antibodies and antibody fragments characteristic of hybridomas of the invention, particularly IC1.11B4.6, can also be produced by recombinant means by extracting messenger RNA, constructing a cDNA library, and selecting clones which encode segments of the antibody molecule, e.g. Wall et al., *Nucleic Acids Research*, Vol. 5, pgs. 3113-3128 (1978) ; Zalsut et al., *Nucleic Acids Research*, Vol. 8, pgs. 3591-3601 (1980); Cabilly et al., *Proc. Natl. Acad. Sci.*, Vol. 81, pgs. 3273-3277 (1984); Boss et al., *Nucleic Acids Research*, Vol. 12, pgs. 3791-3806 (1984); Amster et al., *Nucleic Acids Research*, Vol. 8, pgs. 2055-2065 (1980); and Moore et al., U.S. Pat. No. 4,642,334. In particular, such techniques can be used to produce interspecific monoclonal antibodies, wherein the binding region of one species is combined with non-binding region of the antibody of another species, e.g. Liu et al., *Proc. Natl. Acad. Sci.*, Vol. 84, pgs. 3439-3443 (1987).

Uses of monoclonal antibodies for purification and measurement are well known, e.g. affinity chromatography: *Affinity Chromatography: Principles and Methods* (Pharmacia, Orebro, Sweden, 1979); Secher et al., *Nature*, Vol. 285, pgs. 446-450 (1980), and U.S. Pat. No. 4,423,147; and European patent application 0190711 (13 Aug. 1986); and immunoassay techniques: Tijssen (cited above); U.S. Pat. No. 4,486,530; and Burnette (cited above). Affinity chromatography can be used to purify human IL-4 by extracting it from a sample, such as a culture supernatant of cells transformed or transfected with a human IL-4 expression vector. Such a purification process is referred to herein as an immunopurification process. Typically, it involves covalently attaching a monoclonal antibody specific for human IL-4 to a solid phase support (referred to herein as an "immunoadsorbent") which is placed in a column or chamber through which the sample is passed. Human IL-4 from the sample preferentially binds to the binding sites of the attached monoclonal antibodies, while the rest of the material from the sample is washed from the column or chamber. The human IL-4 is then eluted from the immunoadsorbent by standard techniques, e.g. low pH, high salt concentration, or the like.

"Two site" or "sandwich" immunoassays are the preferred immunoassays of the invention, e.g. as disclosed in U.S. Pat. No. 4,486,530. Accordingly, this patent is incorporated by reference. Such assays entail the use of two different sets of anti-IL-4 antibodies, at least one of which consists of a monoclonal antibody of the invention, such as that produced by IC1.11B4.6. Antibodies from one of the two sets are attached to the surface of a solid phase support. The attached antibodies are then exposed to a sample suspected of containing human IL-4. The IL-4 molecules bind to the attached antibodies. Next, the second set of antibodies is applied to the bound IL-4, and binds to one or more antigenic determinants distinct from that (or those) to which the first set of antibodies is (or are) bound. The IL-4 is then detected by an indirect or direct signal generating means associated with the second set of antibodies. For example, the antibodies can be directly conjugated to a signal generating moiety, such as an enzyme, rare earth chelator, or an organic dye. Or, they can be indirectly linked to one or more signal generating moieties via additional antibodies, or high affinity complexes, such as the avidin-biotin complexes. Quantitative measures of IL-4 concentration are made by comparing the signal generated by the sample to signals generated by IL-4 standards containing known concentrations of human IL-4.

The invention includes kits of reagents for use in immunoassays, particularly sandwich immunoassays. Such kits include (1) a solid phase support, (2) a first antibody which is monoclonal and which is capable of binding to a first antigenic determinant of human IL-4, (3) a second antibody selected from the group consisting of a monoclonal antibody capable of binding to a second antigenic determinant of human IL-4 and a polyclonal antibody specific for human IL-4 (referred to herein as a "polyclonal antibody composition"), and (4) a signal generation means associated with one of the three antibodies. Depending on the particular embodiment, kits may include a selection of two of the three anti-IL-4 antibody types, either a monoclonal antibody specific for a first antigenic determinant and a monoclonal antibody specific for a second antigenic determinant, or a monoclonal antibody specific for a first or second antigenic determinant and a polyclonal antibody composition. The antibodies may be in solution or in lyophilized form. One of the sets of antibodies may come pre-attached to the solid support, or may be applied to the surface of the solid support when the kit is used. The signal generating means may come pre-associated with one of the two antibody types, or may require combination with one or more components, e.g. buffers, antibody-enzyme conjugates, enzyme substrates, or the like, prior to use. Many types of signal generating means are available and could make up one or more components of a kit. Various signal generating means are disclosed by Tijssen (cited above). Kits of the invention may also include additional reagents, e.g. blocking reagents for reducing nonspecific binding to the solid phase surface, washing reagents, enzyme substrates, and the like. The solid phase surface may be in the form of microtiter plates, microspheres, or the like, composed of polyvinyl chloride, polystyrene, or the like materials suitable for immobilizing proteins. Such materials having solid phase surfaces are referred to herein as "support means". Preferably, an enzyme which catalyzes the formation of a fluorescent or colored product is a component of the signal generating means. More preferably, the enzyme is selected from the group consisting of peroxidase, alkaline phosphatase, and betagalactosidase. Substrates and reaction conditions for these enzymes are well known in the art, e.g. Tijssen (cited above).

Compositions of the invention can also be used as components of pharmaceutical compositions directed against IL-4 related diseases. The pharmaceutical compositions can be directed to enhancing IL-4 activity, in the case of monoclonal antibodies, or fragments, having agonistic effects. Or, the compositions can be directed to suppressing IL-4 activity, in the case of monoclonal antibodies, or fragments, having blocking or antagonistic effects. Such compositions contain a therapeutic amount of at least one of the monoclonal antibodies of the invention, or fragments thereof, in a pharmaceutically effective carrier. A pharmaceutical carrier can be any compatible, non-toxic substance suitable for delivering the compositions of the invention to a patient. Sterile water, alcohol, fats, waxes, and inert solids may be included in a carrier. Pharmaceutically accepted adjuvants (buffering agents, dispersing agents) may also be incorporated into the pharmaceutical composition. Generally, compositions useful for parenteral administration of such drugs are well known, e.g. *Remington's*

Pharmaceutical Science, 15th Ed. (Mack Publishing Company, Easton, PA, 1980). Alternatively, compositions of the invention may be introduced into a patient's body by implantable drug delivery systems, e.g. Urquhart et al., Ann. Rev. Pharmacol. Toxicol., Vol. 24, pgs. 199-236 (1984).

EXAMPLES

The following examples serve to illustrate the present invention. Selection of vectors and hosts as well as the concentration of reagents, temperatures, and the values of other variable parameters are only to exemplify application of the present invention and are not to be considered as limitations thereof.

EXAMPLE I

Production of Glycosylated Human IL-4 by Transfection of COS 7 Monkey Cells with pcD-human-IL-4

The expression vector pcD-human-IL-4 and host cell COS 7 are available from the American Type Culture Collection under accession numbers 67029 and CRL 1651, respectively. After amplifying the pcD-human-IL-4 clone, and purifying the plasmid DNA, a standard transfection protocol was used to transfect COS 7: About $1 \times 10^6$ COS 7 cells are seeded onto 100 mm tissue culture plates containing Dulbecco's Modified Eagle's medium (DME), 10% fetal calf serum, and 4 mM L-glutamine. About 24 hours after seeding, the medium is aspirated from the plates and the cells are washed twice with serum free buffered (50 mM Tris) DME. To each plate is added 4 ml serum free buffered DME (with 4 mM L-glutamine), 80 microliters DEAE-dextran, and 5 micrograms of pcD-human-IL-4 DNA. The cells are incubated in this mixture for 4 hours at 30° C., after which the mixture is aspirated off and the cells are washed once with serum free buffered DME. After washing, 5 ml of DME with 4 mM L-glutamine, 100 micromolar chloroquine, and 2% fetal calf serum is added to each plate, the cells are incubated for 3 hours, and then twice washed with serum free buffered DME. Next, 5 ml DME with 4 mM L-glutamine and 4% fetal calf serum is added and the cells are incubated at 37° C. for 24 hours. Afterwards the cells are washed 1-3 times with DME or PBS, 5 ml serum free DME (with 4 mM L-glutamine) is added, and the cells are incubated at 37° C. until culture supernatants are harvested 5 days later.

EXAMPLE II

Purification of Glycosylated Human IL-4 from COS 7 Transfection Supernatants

A. Biological Assay for Purification.

T cell growth factor (TCGF) activity was used to assay human IL-4 during purification from the supernatants produced according to Example I. Several standard assays have been described for TCGF activity, e.g. Devos et al., Nucleic Acids Research, Vol. 11, pgs. 4307-4323 (1983); Thurman et al., J. Biol. Response Modifiers, Vol. 5, pgs 85-107 (1986); and Robert-Guroff et al., Chapter 9 in Guroff, Ed. Growth and Maturation Factors (John Wiley, New York, 1984). Generally, the TCGF assays are based on the ability of a factor to promote the proliferation of peripheral T lymphocytes or IL-2 dependent T cell lines, e.g. Gillis et al. J. Immunol., Vol. 120, pg. 2027 (1978). Proliferation can be determined by standard techniques, e.g. tritiated thymidine incorporation, or by colorimetric methods, Mosmann, J. Immunol. Meth., Vol. 65, pgs. 55-63 (1983). The assay for human IL-4 TCGF activity was carried out as follows: Blood from a healthy donor was drawn into a heparinized tube and layered onto Ficoll-Hypaque; e.g., 5 ml of blood per 3 ml Ficoll-Hypaque in a 15 ml centrifuge tube. After centrifugation at $3000 \times g$ for 20 minutes, cells at the interface were aspirated and diluted in a growth medium consisting of RPMI 1640 containing 10% fetal calf serum, 50 micromolar 2-mercaptoethanol, 20 microgram/ml phytohemagglutinin (PHA), and recombinant human IL-2. After 5-10 days of incubation at 37° C., the PHA-stimulated peripheral blood lymphocytes (PBLs) were washed and used in 2 day colorimetric assays, Mossman, (cited above). Serial two fold dilutions of an IL-4 standard (supernatants from pcD-human-IL-4 transfected COS 7 cells) or the fraction to be tested were performed in 96 well trays utilizing the growth medium described above to yield a final volume of 50 microliters/well. 50 microliters of the PHA stimulated PBLs at about $4-8 \times 10^6$ cells/ml were added to each well and the trays were incubated at 37° C. for 2 days. Cell growth was then measured according to Mosmann (cited above).

One unit, as used herein, is the amount of factor which in one well (0.1 ml) stimulates 50% maximal proliferation of $2 \times 10^4$ PHA stimulated PBLs over a 48 hour period.

B. Purification

Purification was accomplished by a sequential application of cation exchange chromatography, gel filtration and reverse-phase high pressure liquid chromatography. All operations were performed at 4° C.

After removing the COS 7 cells by centrifugation, the supernatant was concentrated about 10 fold by ultrafiltration and stored at −80° C. until further processed. IL-4 titers were determined by assaying for the ability of the protein to stimulate proliferation of phytohemagglutinin-induced human peripheral blood lymphocytes, i.e. by TCGF activity using the standard assay described above.

Concentrated COS 7 supernatant, having TCGF activity of about $10^4$–$10^6$ units/ml and a protein content of about 15-20 mg/ml, is dialyzed against 2 changes of 50 mM sodium HEPES, pH 7.0 over a 24 hour period (each change being approximately 10-15 times the volume of one concentrate). The dialysate was applied to a column ($1 \times 2.5$ cm) of S-Sepharose (flow rate: 0.2 ml/min) pre-equilibrated with 50 mM sodium HEPES, pH 7.0. The column were washed with 15 column volumes of equilibrating buffer followed by elution with 20 column volumes of a linear sodium chloride gradient extending from 0 to 0.5M sodium chloride in 50 mM sodium HEPES, pH 7.0. The gradient was terminated with an isocratic elution consisting of 5 column volumes of 50 mM sodium HEPES, 0.5M NaCl, pH 7.0. 1.5 ml and 1.8 ml fractions were collected from respective batches. IL-4 titers were found for both chromatographies to elute between 300 mM and 500 mM sodium chloride.

The fractions from the S-Sepharose columns containing IL-4 titers were combined for total separate volumes of 9.0 and 10.8 ml. Both volumes were concentrated to 1.9 ml by ultrafiltration using an Amicon YM5 membrane (molecular weight cut-off: 5000). The recovery of protein from this step was about 80%. The concentrated IL-4 solution was applied to a Sephadex G-100 column ($1.1 \times 58$ cm) pre-equilibrated in 50 mM HEPES, 0.4M NaCl, pH 7.0 and the column was eluted with the same buffer at 0.15 ml/min. A total of 50 fractions (1.0 ml/fraction) was collected and analyzed for IL-4 titers. A peak in biological activity was observed at an apparent molecular weight of 22,000 daltons. The Sephadex G-100 was calibrated for apparent molecular determination with bovine serum albumin (65,000 daltons), carbonic anhydrase (30,000 daltons) and cytochrome C (11,700 daltons).

A fraction from the Sephadex G-100 column containing IL-4 activity was concentrated 3-4 fold in vacuo and was injected onto a Vydac C-4 guard column (4.6×20 mm). A linear gradient of 0 to 72% (v/v) acetonitrile in 0.1% (v/v) trifluoroacetic acid (TFA) was produced in 15 minutes at a column temperature of 35° and a flow rate of 1.0 ml/min. Three peaks resulted that were detected at 214 nm with retention times of 7, 8.2 and 8.7 min. (peaks 1, 2, and 3 of FIG. 10, respectively). A 40 microliter aliquot of peak 2 (8.2 min. elution time) was lyophilized and redissolved in minimal essential medium containing 10% fetal calf serum. This solution showed a positive TCGF response. A 300 microliter aliquot of peak 2 was evaporated to dryness and redissolved in 200 ul of 0.1% (w/v) sodium dodecyl sulfate (SDS). A 2 ul aliquot was diluted in 200 ul of 1% (v/v) TFA and rechromatographed. The HPCL of this sample demonstrated a single peak at 215 nm. Peak 2 material indicated an activity of about $7 \times 10^8$ units/mg.

EXAMPLE III

Production of Unglycosyalted Human IL-4 in Escherichia coli

An *E. coli* expression vector, denoted TRPC11, was constructed using standard techniques, e.g. as disclosed in Maniatis et al., *Molecular Cloning: A Laboratory Manual* (Cold Spring Harbor Laboratory, New York, 1982).

The TRPC11 vector was constructed by ligating a synthetic consensus RBS fragment to ClaI linkers (ATGCAT) and by cloning the resulting fragments into ClaI restricted pMT11hc (which had been previously modified to contain the ClaI site). pMT11hc is a small (2.3 kilobase) high copy, $AMP^R$, $TET^S$ derivative of pBR322 that bears the $\pi$VX plasmid (described by Maniatis et al., cited above) EcoRI-HindIII polylinker region. It was modified to contain the ClaI site by restricting pMT11hc with EcoRI and BamHI, filling in the resulting sticky ends and ligating with ClaI linker (CATCGATG), thereby restoring the EcoRI and BamHI sites and replacing the SmaI site with a ClaI site.

One transformant from the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI, and treating with T4 DNA polymerase in the presence of all four deoxynucleotide triphosphates. The resulting 30-40 bp fragments were recovered via polyanylamide gel electrophoresis and cloned into SmaI restricted pUC12. A 248 bp *E. coli* trpP-bearing EcoRI fragment derived from pKC101 (described by Nichols et al. in *Methods in Enzymology*, Vol. 101, pg. 155 (Academic Press, New York 1983)) was then cloned into the EcoRI site to complete the TRPC11 construction, which is illustrated in FIG. 1.

TRPC11 was employed as a vector for human IL-4 cDNA by first digesting it with ClaI and BamHI, purifying it, and then mixing it with the EcoRV/BamHi fragment of pcD-125 (deposited with the ATCC under accession number 67029) in a standard ligation solution containing 0.1 micromolar of the following synthetic linker:

```
5'-CG ATG CAC AAG TGC GAT-3'
   TAC GTG TTC ACG CTA
```

*E. coli* AB1899 were transformed directly with the ligation solution using the standard calcium chloride procedure, propagated, and plated. Colonies containing the IL-4 cDNA insert were selected using a labeled oligonucleotide probe. The transformants were cultured in L-broth, and IL-4 was expressed constitutively.

EXAMPLE IV

Purification of Unglycosylated Human IL-4 from Aggregates Produced by Escherichia coli A 1 liter culture of *E. coli* AB1899 (lon-) (obtained from Yale University *E. coli* Genetics Center, New Haven Conn.) was grown to $OD_{560}=2$ (about $1.6 \times 10^9$ cells/ml). Cells were harvested by centrifugation at 4500 Xg for 15 minutes at 4° C. The pellets were resuspended in 30 ml of 50 mM Tris buffer, pH 8.0, containing 50 mM NaCl, 1 mM ethylenediaminetetraacetic acid (EDTA), and 0.1 mM phenylmethylsulfenyl fluoride (PMSF). EDTA and PMSF are added to inhibit protease activity which might degrade the human IL-4 before purification. Next, the cells were sonicated, 50 pulses (50%) at 70 watts, and centrifuged, 25,000 Xg for 15 minutes at 4° C. The major protein component of the resulting pellet was shown to be IL-4 by comparing the gel band pattern of electrophoretically separated pellet material (which had been solubilized in sodium dodecylsulphate (SDS) and stained with Coomassie Blue), with a negative control.

After removal of the supernatant, pellet material was resuspended (9 ml for each gram of pellet material in Tris buffer solution (50 mM Tris, 50 mM NaCl, 1 mM EDTA, 0.1 mM PMSF, pH 8.0) containing 5M guanidine HCl, 2 mM glutathione (reduced form), and 0.2 mM glutathione (oxidized form). After approximately 1 hour at room temperature, the solution was diluted 1:9 into a Tris buffer solution, pH 8.0, containing 2 mM glutathione (reduced form) and 0.2 mM glutathione (oxidized form). Whenever precipitates occurred during the dilution, dialysis, or concentration steps, they were removed by centrifugation before proceeding. The entire volume was then dialyzed overnight 3 times against 3 liters of phosphate buffer solution. The dialyzate (i.e. the material retained by the dialysis bag) was concentrated by an Amicon YM5 filter (final concentration 8 mg/ml), and subjected to gel filtration chromatography (column: P30 (BioRad), 1.5×90 cm; PBS elution buffer; flow rate: 8 ml/hr). Fractions were collected over 15 minute intervals. Fractions 23-27 were pooled and further analyzed by reverse phase HPLC. Such analysis indicated that the pooled factions contained >95% pure human IL-4. The yield from the 1 liter culture ($OD_{560}$ of 2) was 2 mg of human IL-4 with a specific activity of $5 \times 10^7$ units/mg.

EXAMPLE V

Production of Hybridoma IC1.11B4.6

A male Lewis rat was immunized intraperitoneally (i.p.) with 1 ml of human IL-4 solution emulsified with 1 ml complete Freund's adjuvant (CFA). The human IL-4 solution consisted of human IL-4 at concentration of 14 μg/ml in 10 mM Tris-HCl, 0.5M NaCl, pH 7.4. The human IL-4 was produced in accordance with Examples I and II, and had a specific activity of $2 \times 10^7$ units/mg. Two weeks after the initial immunization, the rat was against injected i.p. with 1 ml human IL-4 solution emulsified with 1 ml CFA. Three months after the second injection, the rat was boosted intravenously with 1 ml human IL-4 solution (15 μg). Four days after the booster injection the rat was sacrificed, blood was collected, and the spleen was removed for fusion. Spleen cells were fused with mouse myeloma cells, P3X63-Ag8.653 (ATCC CRL 1580), in a 1:1 ratio using polyethylene glycol (PEG). The cell suspension ($3.5 \times 10^5$ cells/ml in HAT medium was distributed into 40 96-well plates. Ten days later hybridoma supernatants were tested for their ability to bind to human IL-4 immobilized directly on microtiter plates (indirect ELISA), or to human IL-4 bound to immobilized polyclonal IgG fraction of rabbit anti-human IL-4. Bound antibody was detected by peroxidase conjugated goat anti-rat immunoglobulin with a standard protocol. Hybridomas secreting antibodies reacting with IL-4 were cloned by limiting dilution. IC1.11B4.6 was one such hybridoma selected by these procedures. Antibodies from IC1.11B4.6 were determined to be of the $IgG_{2a}$ isotype. The hybridoma is stored (e.g. −70° C. in culture medium with 10% DMSO) and cultured using standard mammalian cell culture techniques (e.g., RPMI 1640 with 10% fetal bovine serum, supplemented with 1 mM glutamine and 50 mM 2-mercaptoethanol).

EXAMPLE VI

Sandwich Assay for Human IL-4

100 μl of rabbit polyclonal anti-human IL-4 antibody (10 μg/ml in PBS purified on a protein A affinity column is adsorbed onto the surface of each well in a 96-well polyvinyl chloride microtiter plate for 2 hrs. at 37° C. (PBS consists of 8.0 g of NaCl, 0.2 g of $KH_2PO_4$, 2.9 g of $Na_2HPO_4.12H_2O$, and 0.2 g of KCl, in 1 liter of distilled water. The pH is 7.4). After washing the plate with PBS-Tween (prepared exactly as PBS, except that 0.5 ml of Tween 20 is added per liter) to remove unbound antibody, duplicate serial dilutions (in PBS) of purified E. coli-produced human IL-4 are placed in two 12-well rows of wells in order of decreasing IL-4 concentrations, which range from 1000 pg/ml to 15 pg/ml. The following samples were loaded into the remaining wells: (1) culture supernatants from a human T cell clone, e.g. ClLy1+2−/9 (ATCC CRL 8179), (2) culture supernatants of COS 7 cells transfected with pcD-human-IL-4, (3) human serum containing different concentrations of purified COS7-produced IL-4, and (4) samples containing human IL-1α, IL-2, IL-3, IFN-γ, IFN-α2b, GM-CSF, and BSF-2. All of the samples were incubated for 2 hours at room temperature. After washing with PBS-Tween, a 1:10 dilution of supernatant from a culture of IC1.11B4.6 was added to each well (100 μl/well) and was allowed to incubate for 1 hour at room temperature. After incubation, the plate was washed and peroxidase conjugated goat antirat antibody was added and allowed to incubate for 1 hour at room temperature, after which the plate was washed. Next, the peroxidase substrate ABTS was added, and the human IL-4 (analyte) concentrations were related to optical densities in the wells. The results indicate that the assay can detect mammalian-produced human IL-4 at concentrations as low as 50 pg/ml in human serum, and that the assay does not detect any of the lymphokines listed above.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Applicants have deposited hybridoma IC1.11B4.6 with the American Type Culture Collection, Rockville, Md., USA (ATCC), under accession number HB9550. This deposit was made under conditions as provided under ATCC's agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

We claim:

1. A monoclonal antibody which specifically binds to human interleukin-4.

2. A hybridoma which produces monoclonal antibodies which bind specifically to human interleukin-4.

* * * * *